(12) United States Patent
Murata et al.

(10) Patent No.: US 7,642,370 B2
(45) Date of Patent: Jan. 5, 2010

(54) METHOD FOR PREPARING PROSTAGLANDIN DERIVATIVE

(75) Inventors: Noriaki Murata, Izumi (JP); Atsunori Aramata, Takaoka (JP)

(73) Assignee: Daiichi Fine Chemical Co., Ltd., Toyama (JP)

(*) Notice: Subject to any disclaimer, the term of this patent is extended or adjusted under 35 U.S.C. 154(b) by 0 days.

(21) Appl. No.: 11/688,566

(22) Filed: Mar. 20, 2007

(65) Prior Publication Data

US 2008/0033176 A1 Feb. 7, 2008

Related U.S. Application Data

(60) Provisional application No. 60/835,909, filed on Aug. 7, 2006.

(51) Int. Cl.
C07C 69/527 (2006.01)

(52) U.S. Cl. .......................................... 560/61; 562/471

(58) Field of Classification Search ................. 549/263, 549/305, 295, 311; 560/121, 61; 562/503, 562/471

See application file for complete search history.

(56) References Cited

U.S. PATENT DOCUMENTS

| | | | |
|---|---|---|---|
| 3,892,795 A | 7/1975 | Magerlein | |
| 3,971,826 A | 7/1976 | Hess et al. | |
| 4,284,581 A | 8/1981 | Noyori | |
| 4,792,617 A | 12/1988 | Cooper et al. | |
| 4,824,857 A | 4/1989 | Goh et al. | |
| 5,359,095 A | 10/1994 | Resul | |
| 5,466,833 A | 11/1995 | Ivanics et al. | |
| 6,689,901 B2 | 2/2004 | Henegar | |
| 7,163,959 B2 | 1/2007 | Stjernschantz et al. | |
| 2004/0249172 A1 | 12/2004 | Greenwood et al. | |
| 2005/0261374 A1 | 11/2005 | Greenwood et al. | |
| 2005/0272877 A1 | 12/2005 | Greenwood et al. | |
| 2006/0079693 A1 | 4/2006 | Suen et al. | |

FOREIGN PATENT DOCUMENTS

| | | |
|---|---|---|
| CZ | 287482 | 10/2000 |
| EP | 0170258 | 2/1986 |
| EP | 0253094 | 1/1988 |
| EP | 0362686 | 4/1990 |
| GB | 1372541 | 10/1974 |
| JP | 48-18259 | 3/1973 |
| JP | 55051093 A * | 4/1980 |
| JP | 61-2049 | 1/1986 |
| JP | 62-36012 | 8/1987 |
| WO | 90/02553 | 3/1990 |
| WO | 92/02496 | 2/1992 |
| WO | 93/00329 | 1/1993 |
| WO | 01/55101 | 8/2001 |
| WO | 02/096898 | 12/2002 |
| WO | WO 02/096898 A2 * | 12/2002 |
| WO | 03/008368 | 1/2003 |
| WO | 2005/058812 | 6/2005 |

OTHER PUBLICATIONS

Resul et al., J. Med. Chem. 1993, 36, 243-248.*
Corey et al., "Stereo-Controlled Synthesis of Prostaglandins $F_{2\alpha}$ and $E_2$ (dl)", J. Am. Chem. Soc., vol. 91, No. 20, pp. 5675-5677 (1969).
Corey et al., "Efficient Generation of the 15S Configuration in Prostaglandin Synthesis. Attractive Interactions in Stereochemical Control of Carbonyl Reduction", J. Am. Chem. Soc., vol. 94, No. 24, pp. 8616-8618 (1972).
Noyori et al., "Synthetic Applications of the Enantioselective Reduction by Binaphthol-Modified Lithium Aluminum Hydride Reagents", J. Am. Chem. Soc., vol. 106, pp. 6717-6725 (1984).
Green et al., "Protective Groups in Organic Syntheses". John-Wiley and Sons, Inc., pp. 48-55, 76-87, 126-141, 150-161, 172-179, 206-215, 296-309, 518-537, 552-561, and 578-581.
An English language abstract (of corresponding Japanese Publication No. JP 55-1429217, published Nov. 20, 1980).
An English language abstract (of corresponding Japanese Publication No. JP 55-051093, published Apr. 14, 1980).
Resul et al., "Phenyl-Substituted Prostaglandins: Potent and Selective Antiglaucoma Agents", Journal of Medicinal Chemistry, vol. 36, No. 2., pp. 243-248(1993).
US 6,720,438, 04/2004, Gutman et al. (withdrawn)

* cited by examiner

*Primary Examiner*—Bernard Dentz
*Assistant Examiner*—David E Gallis
(74) *Attorney, Agent, or Firm*—Greenblum & Bernstein, P.L.C.

(57) ABSTRACT

A method for preparing a prostaglandin derivative represented by the following general formula (I):

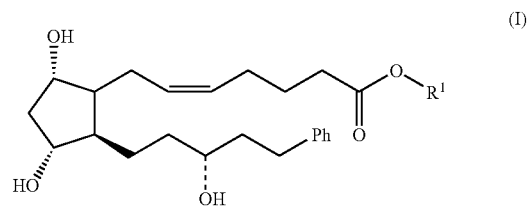

(wherein Ph represents phenyl group, $R^1$ represents a $C_{1-7}$ alkyl group, a $C_{1-7}$ alkenyl group, phenyl group, or benzyl group), which comprises the successive steps (1) to (8) described in the specification, or any one step or two or more successive steps selected from the group consisting of the steps (1) to (8). A method for efficiently, inexpensively and safely preparing prostaglandin derivatives, of which typical example is latanoprost, is provided.

4 Claims, No Drawings

METHOD FOR PREPARING PROSTAGLANDIN DERIVATIVE

This application claims the benefit of U.S. Provisional Application No. 60/835,909, filed on Aug. 7, 2006, which is incorporated by reference herein in its entirety.

TECHNICAL FIELD

The present invention relates to a method for preparing a prostaglandin derivative such as latanoprost.

BACKGROUND ART

It has been known that, among prostaglandin derivatives, there are many derivatives that reduce ocular tension when they are topically applied (EP 0170258 and EP 0253094), and it has been reported that, among 13,14-dihydro-17-phenyl-18,19,20-trinor-PGF2α-isopropyl esters, an optically active substance represented by the following formula (hereinafter, this compound is referred to as "latanoprost") has high efficacy and can be used as a therapeutic agent for glaucoma (WO90/02553).

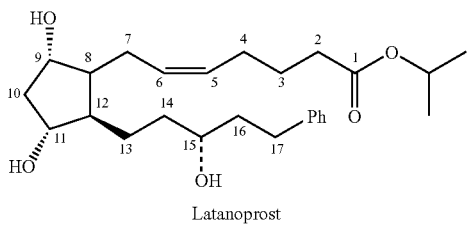

Latanoprost

Since latanoprost has a chemical structure similar to that of prostaglandin F2α, a preparation method based on the Corey method (J. Am. Chem. Soc., 91(20), pp. 5675-5677, 1969) has been proposed for the synthesis thereof (method of preparing latanoprost from so-called Corey lactone). The key steps for preparing latanoprost by this method are (1) protection of hydroxyl groups at the positions corresponding to the 11th and 15th positions of latanoprost, (2) introduction of a specific configuration ((R)-configuration) of the hydroxyl group at the position corresponding the 15th position of latanoprost, and (3) introduction of a single bond linking 13th and 14th positions of latanoprost.

In relation to these steps, WO92/02496 discloses a method of protecting hydroxyl groups at the positions corresponding to the 11th and 15th positions of latanoprost, and then hydrogenating the double bonds to form a single bond linking 13th and 14th positions of latanoprost.

WO93/00329 discloses a method of introducing a carboxyalkenyl group at the position corresponding to the 8th position of latanoprost as a side chain (skeleton of the 1st to 7th positions) without protecting the hydroxyl groups at the positions corresponding to the 11th and 15th of latanoprost.

WO03/08368 discloses a method of using a boron asymmetric reducing reagent and (-)-chlorodiisopinocamphenylborane to introduce hydroxyl group of a specific configuration at the 15th position of latanoprost and utilizing a ring-opened lactone as a preparation intermediate.

WO01/55101 discloses a method of introducing a carboxyalkenyl group at a position corresponding to the 8th position of latanoprost as a side chain (skeleton of the 1st to 7th positions) without protecting the hydroxyl group at the position corresponding to the 11th position of latanoprost.

US 2006/0079693 discloses a method of using a compound introduced with 3-oxo-5-phenyl-1,4-pentadienyl group as a side chain (skeleton of the 13th to 17th positions) at the position corresponding to the 12th position of latanoprost as a preparation intermediate.

Further, although not methods for preparing latanoprost per se, methods for preparing compounds that can be used as a precursor thereof are also known.

For example, a method of preparing 13,14-dihydro-17-phenyl-18,19,20-trinor-PGF2α from the Corey lactone is disclosed in Japanese Patent Unexamined Publication (Kokai) No. 48-18259, Example 3, No. 1, and a method of preparing 11,15-bistetrahydropyranyloxy-13,14-dihydro-17-phenyl-18,19,20-trinor-PGF2α from the Corey lactone is disclosed in Examples 3 to 7 and Example 25 of U.S. Pat. No. 3,971,826.

These preparation methods have problems that they are comprised of many steps although they have minor differences, and that target substance cannot be obtained in a total yield that is industrially satisfactory. In particular, when a reducing agent that does not have asymmetric distinguishability is used in the step of introducing hydroxyl group in a specific configuration at the position corresponding to the 15th position of latanoprost, a problem of heavy burden arises in later separation steps. They also have problems of using an expensive reagent such as (-)-chlorodiisopinocamphenylborane for asymmetric reduction, or a large amount of a reagent required for a substrate. Furthermore, they also have problems of using a dangerous raw material such as diisobutylaluminum hydride or readily occurred side reactions mainly at unprotected positions.

Non-patent document 1: J. Am. Chem. Soc., 91(20), pp. 5675-5677, 1969

Patent document 1: International Publication WO90/02553
Patent document 2: International Publication WO92/02496
Patent document 3: International Publication WO93/00329
Patent document 4: International Publication WO03/08368
Patent document 5: International Publication WO01/55101
Patent document 6: U.S. Patent Application Publication No. 2006/0079693
Patent document 7: Japanese Patent Unexamined Publication No. 48-18259

DISCLOSURE OF THE INVENTION

Object to be Achieved by the Invention

An object of the present invention is to provide a method for efficiently, inexpensively and safely preparing prostaglandin derivatives, of which typical example is latanoprost.

Means for Achieving the Object

The inventors of the present invention conducted various researches to achieve the foregoing object. As a result, they found that prostaglandin derivatives including latanoprost were successfully prepared in extremely efficient, inexpensive and safe manners by the following steps, and accomplished the present invention.

The present invention thus provides a method for preparing a prostaglandin derivative represented by the following general formula (I):

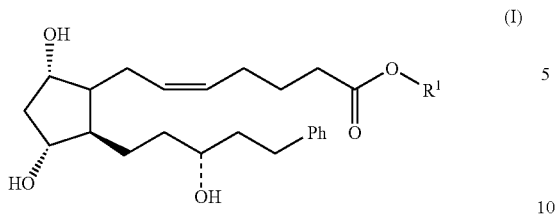

(I)

(wherein Ph represents phenyl group, $R^1$ represents a $C_{1-7}$ alkyl group, a $C_{1-7}$ alkenyl group, phenyl group, or benzyl group), which comprises the following steps:

(1) the step of converting a compound represented by the following formula (II) (X represents a protective group selected from the group consisting of an aroyl group having 0 to 3 substituents, a trialkylsilyl group, a triarylsilyl group, and tetrahydroxypyranyl group, wherein the substituents of the aroyl group are selected from the group consisting of a halogen atom, a $C_{1-6}$ alkyl group and a $C_{6-12}$ aryl group) into a compound represented by the following formula (IV) by oxidizing the compound of the formula (II) into an aldehyde and then reacting the aldehyde with a phosphonic acid ester represented by the following formula (III) ($R^2$ represents a $C_{1-6}$ alkyl group or a $C_{6-12}$ aryl group);

(2) the step of converting the compound represented by the following formula (IV) into a compound represented by the following formula (V) by reducing the oxo group on the side chain of the compound of the formula (IV);

(3) the step of converting the compound represented by the following formula (V) into a compound represented by the following formula (VI) by hydrogenating the compound of the formula (V);

(4) the step of converting the compound represented by the following formula (VI) into a compound represented by the following formula (VII) by removing the protective group X of the compound of the formula (VI);

(5) the step of converting the compound represented by the following formula (VII) into a compound represented by the following formula (VIII) by protecting the hydroxyl groups of the compound of the formula (VII) with protective groups P, wherein the protective group P is different from the protective group X, and selected from the group consisting of a trialkylsilyl group, a triarylsilyl group and tetrahydroxypyranyl group;

(6) the step of converting the compound represented by the following formula (VIII) into a compound represented by the following formula (IX) by reducing the oxo group on the lactone ring of the compound of the formula (VIII);

(7) the step of converting the compound represented by the following formula (IX) into a compound represented by the following formula (X) by reacting the compound of the formula (IX) with a 4-carboxybutyltriphenylphosphonium halide; and (8) the step of converting the compound represented by the following formula (X) into a compound represented by the following formula (XI) by esterifying the carboxyl group of the compound of the formula (X) and then removing the protective groups P.

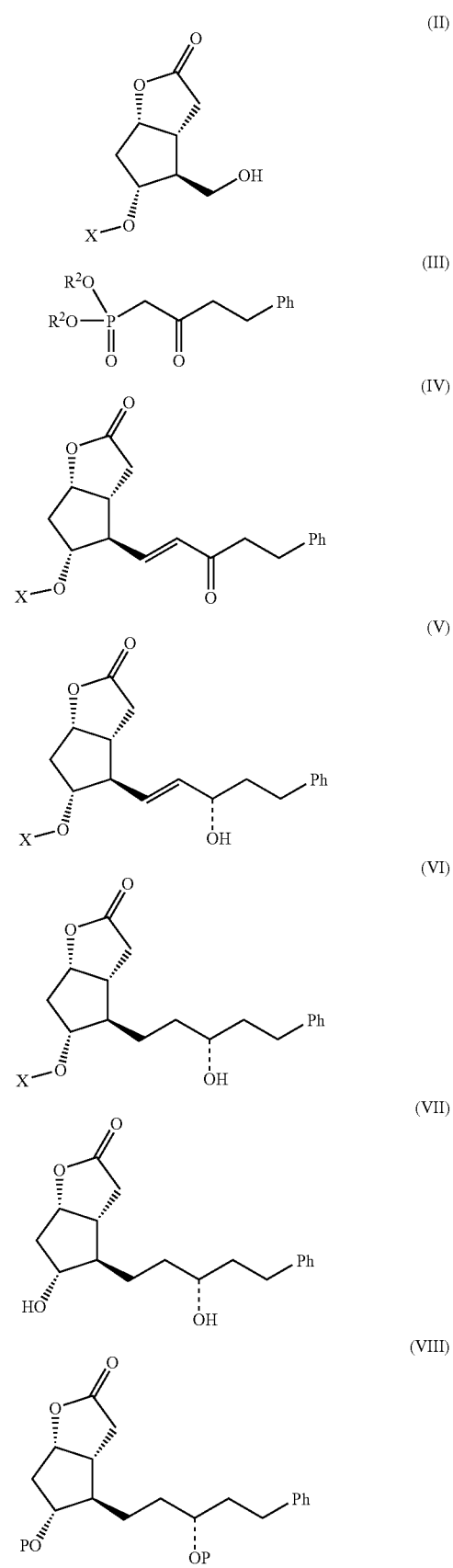

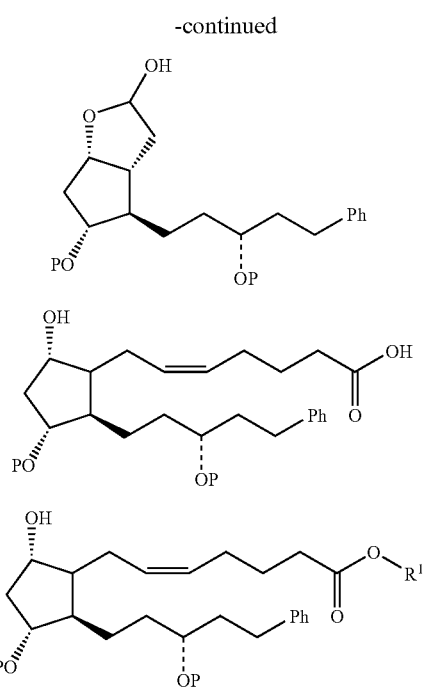

(in the above formulas (III) to (XI), Ph represents phenyl group).

According to preferred embodiments of the present invention, provided are the aforementioned method, wherein X is benzoyl group, and/or P is tetrahydroxypyranyl group, and $R^1$ is isopropyl group; and the aforementioned method, wherein asymmetric reduction is performed in the aforementioned step (2) by using (S)-1,1'-binaphthyl-2,2'-dioxyaluminum hydride as a reducing agent.

The present invention also provides a method for preparing a prostaglandin derivative represented by the aforementioned general formula (I), which comprises any one step or two or more successive steps selected from the group consisting of the aforementioned steps (1) to (8).

From another aspect of the present invention, there is also provided a compound for use as an intermediate for preparing a prostaglandin derivative represented by the aforementioned general formula (I), which is selected from the group consisting of compounds represented by formulas (IV), (V), (VI), (VII), (VIII), (IX), (X) and (XI) mentioned in claim 1.

EFFECT OF THE INVENTION

According to the preparation method of the present invention, prostaglandin derivatives represented by the general formula (I) can be efficiently and inexpensively prepared by safer steps in a high yield.

BEST MODE FOR CARRYING OUT THE INVENTION

In the general formula (I), $R^1$ represents a $C_{1-7}$ alkyl group, a $C_{1-7}$ alkenyl group, phenyl group, or benzyl group. As the alkyl group, a straight, branched or cyclic alkyl group or an alkyl group consisting of a combination thereof can be used, and a straight or branched alkyl group is preferred. A branched alkyl group is more preferred, and isopropyl group is particularly preferred. Although number of double bonds contained in the alkenyl group is not particularly limited, the number is usually around 1 or 2. Steric configurations of double bonds are not particularly limited, and the compound may be a Z- or E-stereoisomer.

In the step (1) of the method of the present invention, the Corey lactone represented by the formula (II), which is widely used as an intermediate for synthesis of naturally occurring prostaglandins, can be used as a starting material. As X, a protective group selected from the group consisting of an aroyl group having 0 to 3 substituents, a trialkylsilyl group, a triarylsilyl group, and tetrahydroxypyranyl group may be used. As the aroyl group, benzoyl group, naphthoyl group, and the like may be used. When the aroyl group has a substituent, the substituent is selected from the group consisting of a halogen atom, a $C_{1-6}$ alkyl group and a $C_{6-12}$ aryl group. Position of the substituent on the aromatic ring is not particularly limited, and when the group has two or more substituents, they may be the same or different. The halogen atom is selected from fluorine atom, chlorine atom, bromine atom, and iodine atom. As the $C_{1-6}$ alkyl group, a straight, branched or cyclic alkyl group or an alkyl group consisting of a combination thereof may be used. Examples of the $C_{6-12}$ aryl group include phenyl group, naphthyl group, and the like. Examples of the trialkylsilyl group include trimethylsilyl group, tert-butyldimethylsilyl group, and the like. Examples of the triarylsilyl group include triphenylsilyl group, and the like. As X, an aroyl group is preferred, an unsubstituted aroyl group is more preferred, and benzoyl group is particularly preferred. A preferred compound represented by the formula (II) is [3aR-(3aα,4α,5α,6aα)]-5-(benzoyloxy)hexahydro-4-(hydroxymethyl)-2H-cyclopenta[b]furan-2-one, and it can be obtained by, for example, the method described in U.S. Pat. No. 3,892,795.

The compound represented by the formula (IV) can be obtained by, for example, oxidizing a compound represented by the formula (II) wherein X is benzoyl group to convert the compound to an aldehyde and then performing, for example, the Horner-Emmons reaction with dimethyl (2-oxo-4-phenylbutyl)phosphate under a basic condition. The method for the oxidation into an aldehyde is not particularly limited, and may be any of methods available for those skilled in the art, and examples thereof include, for example, a method of using 1,3-diisopropylcarbodiimide or dicyclohexylcarbodiimide in dimethyl sulfoxide, and the like. In the oxidation reaction, more favorable results may be obtained by adding orthophosphoric acid. Although the reaction conditions are not particularly limited, the reaction can be performed, for example, at 20 to 50° C. for about 0.5 to 5 hours, and it is preferable to use 1,3-diisopropylcarbodiimide or dicyclohexylcarbodiimide in an amount of about 1 to 5 molar equivalents and orthophosphoric acid in an amount of about 0.1 to 1 molar equivalent based on the compound represented by the formula (II). To prepare the basic condition for the Horner-Emmons reaction, for example, alkali metal alcoholates, organic amines, and the like can be used, and triethylamine is preferably used. In this reaction, it is also preferable to add an alkali metal salt such as lithium chloride. Although type of the solvent used for the Horner-Emmons reaction is not particularly limited, for example, methylene chloride, tetrahydrofuran, a mixed solvent thereof, and the like can be preferably used. Although the reaction conditions are also not particularly limited, the reaction can be performed, for example, at −25 to 25° C. for 0.5 to 5 hours, and it is preferable to use dimethyl (2-oxo-4-phenylbutyl)phosphate in an amount of about 1 to 3 molar equivalents, an organic amine in an amount of about 1 to 3 molar equivalents, and lithium chloride in an amount of about 1 to 3 molar equivalents based on the compound represented by the formula (II).

In the step (2), the oxo group on the side chain of the compound represented by the formula (IV) can be reduced by using, for example, a reagent suitable for the enone reduction described in, for example, publications concerning preparation of prostaglandins (the "side chain" means 5-phenyl-3-oxo-1-pentenyl group binding to the bicyclic structure containing the lactone ring). More specifically, examples of the regent include borohydride compounds such as lithium tri-sec-butyl-borohydride and sodium borohydride, lithium aluminum hydride, and the like (J. Am. Chem. Soc., 94, 861, 1972; J. Am. Chem. Soc., 106, 6717, 1984). When the oxo group is reduced, a mixture of 2 types of diastereomers in which the hydroxyl group at the position corresponding to the 15th position of latanoprost is in the (R)-configuration and (S)-configuration may be obtained. In the method of the present invention, the optical isomer used in the following step is a compound in which the hydroxyl group at the position corresponding to the 15th position of latanoprost has (R)-configuration (optically active substance represented by the aforementioned formula (V)), and therefore, in the preparation as mentioned above, it is necessary to subject the product obtained by the reduction to a separation/purification operation such as column chromatography or recrystallization as required to obtain a compound represented by the formula (V) as the objective substance.

In order to avoid the aforementioned separation/purification step, the oxo group is preferably reduced in a stereoselective manner. Examples of the stereoselective reduction include reduction using enzymes and microorganisms, reduction using an asymmetric reagent such as (−)-chlorodiisopinocamphenylborane, and the like. (S)-1,1'-Binaphthyl-2-2'-dioxyaluminum hydride, which is a hydride complex prepared by reacting equivalents of (S)-1,1-bi-2-naphthol, ethanol and hydride lithium aluminum, can be preferably used (U.S. Pat. No. 428,581 and Japanese Patent Publication (Kokoku) Nos. 61-2049 and 62-36012). Although the solvent is not particularly limited, methylene chloride, tetrahydrofuran, or a mixed solvent thereof can be preferably used, for example. Although the reaction conditions are also not particularly limited, the reaction can be performed, for example, at −80 to −50° C. for 0.5 to 5 hours, and it is preferable to use (S)-1,1-bi-2-naphthol, ethanol and lithium aluminum hydride in an amount of about 1 to 10 molar equivalents each based on the compound represented by the formula (IV).

According to the step (3), the compound represented by the formula (V) can be converted into a compound represented by the formula (VI) by hydrogenation. The hydrogenation can be performed in the presence of a catalyst usually used for hydrogenation. Examples of the catalyst include palladium/activated carbon, platinum/activated carbon, rhodium/activated carbon, and the like, and palladium/activated carbon is preferred. The aforementioned hydrogenation reaction is preferably performed in the presence of a basic substance, and as a basic substance, for example, triethylamine and the like can be used. Although type of the solvent is not particularly limited, methylene chloride, tetrahydrofuran, ethyl acetate, or a mixed solvent thereof can be preferably used, for example. Although the reaction conditions are not also particularly limited, the reaction can be performed, for example, at 0 to 40° C. for 1 to 10 hours, the catalyst such as palladium/activated carbon can be used in an amount of about 0.05 to 2 parts by mass for 1 part by mass of the compound represented by the formula (V), and the basic substance such as triethylamine can be used in an amount of about 0.1 to 1 part by volume for 1 part by volume of the compound represented by the formula (V).

According to the step (4), a compound represented by the formula (VII) can be prepared by deprotecting the compound represented by the formula (VI). For the deprotection reaction, a suitable method can be selected depending on the type of the protective group X. As for the conditions of removal of the protective group, for example, Theodora W Green et al., "Protective Groups in Organic Syntheses," John Wiley & Sons, Inc., and the like can be referred to. For example, when X is benzoyl group, deprotection can be attained by reacting a basic substance, for example, an alkali metal salt such as potassium carbonate, in a protic solvent such as methanol. Although the reaction conditions are not particularly limited, the reaction can be performed at 5 to 40° C. for 1 to 5 hours, and potassium carbonate can be used in an amount of about 1 to 20 molar equivalents based on the compound represented by the formula (VI).

According to the step (5), a compound represented by the formula (VIII) can be prepared by introducing a protective group P into the compound represented by the formula (VII). The introduction reaction of the protective group can be properly selected depending on the type of the protective group P, and for the reaction conditions, the aforementioned publication of Green et al. can be referred to. As the protective group P, tetrahydropyranyl group is preferred. When the protective group P is tetrahydropyranyl group, the protective group can be introduced by reacting dihydropyrane in the presence of an acid or a salt thereof, for example, hydrochloric acid, sulfuric acid, p-toluenesulfonic acid, pyridinium p-toluenesulfonate, or the like. Although type of the solvent is not particularly limited, methylene chloride, tetrahydrofuran, and the like can be preferably used, for example. Although the reaction conditions are also not particularly limited, the reaction can be performed, for example, at 5 to 40° C. for 1 to 10 hours, and it is preferable to use dihydropyrane in an amount of about 2 to 5 molar equivalents, and pyridinium p-toluenesulfonate in an amount of about 0.01 to 0.2 molar equivalents based on the compound represented by the formula (VII).

According to the step (6), a compound represented by the formula (IX) can be prepared by reducing the oxo group on the lactone ring of the compound represented by the formula (VIII). Although type of the reducing agent used for the reduction of the oxo group on the lactone ring is not particularly limited, diisobutylaluminum hydride, sodium bis(2-methoxyethoxy)aluminum hydride (i.e., Vitride reagent), and the like can be used, for example, and sodium bis(2-methoxyethoxy)aluminum hydride is preferably used. The aforementioned reduction reaction can be performed according to, for example, the methods described in European Patent No. 362686, CZ 287482 and the like. Although type of the solvent is not particularly limited, for example, toluene is preferred. Although the reaction conditions are also not particularly limited, the reaction is preferably performed, for example, at −90 to −50° C. for 1 to 10 hours, and it is preferable to use sodium bis(2-methoxyethoxy)aluminum hydride in an amount of about 0.5 to 3 molar equivalents based on the compound represented by the formula (VIII).

The compound represented by the formula (IX) can be converted into a compound represented by the formula (X) by the Wittig reaction, and the reaction can be performed by using a base and solvent usually used for the Wittig reactions. As the base, for example, sodium amide, potassium tertiary butyrate, sodium hydroxide and butyl lithium can be preferably used, and as the solvent, diglyme, dimethyl sulfoxide, dimethylformamide, tetrahydrofuran and the like are preferred. As the Wittig reagent, for example, (4-carboxybutyl) triphenylphosphonium bromide can be used. Although the reaction conditions are not particularly limited, the Wittig reagent is preferably used in an amount of about 1 to 5 molar equivalents, and the base is preferably used in an amount of about 1 to 10 molar equivalents based on the compound represented by the formula (IX).

The compound represented by the formula (X) can be appropriately converted into a compound represented by the formula (XI) by using a method ordinarily used as an ester synthesis method depending on the type of a target ester. For example, in order to produce an alkyl ester, it is preferable to react an alkyl iodide with the compound represented by the formula (X). For example, to produce a latanoprost in which $R^1$ is isopropyl group, isopropyl iodide can be used in the presence of cesium carbonate. Although type of the solvent is not particularly limited, dimethylformamide can be preferably used. Although the reaction conditions are also not particularly limited, the reaction can be performed, for example, at 10 to 50° C. for 1 to 10 hours, and it is preferable to use an alkyl iodide in an amount of 1 to 5 molar equivalents, and a base such as cesium carbonate, if necessary, in an amount of 1 to 5 molar equivalents based on the compound represented by the formula (X).

The deprotection reaction of the compound represented by the formula (XI) can be properly performed depending on the type of the protective group, and for example, Theodora W, Green et al., "Protective Groups in Organic Syntheses," John Wiley & Sons, Inc. and the like can be referred to. When the protective group P is tetrahydropyranyl group, the deprotection can be performed by acidification, namely, the deprotection can be performed, for example, in the presence of p-toluenesulfonic acid. Although type of the solvent is not particularly limited, for example, ethanol, isopropanol, a mixture thereof, and the like can be preferably used. Although the reaction conditions are not also particularly limited, the reaction can be performed, for example, at 20 to 60° C. for 1 to 10 hours, and an acid is preferably used in an amount of about 0.01 to 0.3 molar equivalents based on the compound represented by the formula (X).

In the aforementioned steps (1) to (8), an operation for separation or purification of an objective substance or intermediate in each step may be added. For example, a purification operation by a usual means such as column chromatography or recrystallization may be added. Alternatively, an objective substance obtained in each step may be used as a raw material for the following step without purification.

In addition to the method in which the aforementioned steps (1) to (8) are performed successively, methods of performing any one step of the aforementioned steps (1) to (8) or 2 to 7 successive steps among the aforementioned steps (1) to (8) also fall within the scope of the present invention. Further, the compounds represented by the aforementioned formulas (IV), (V), (VI), (VII), (VIII), (IX), (X) and (XI) can be used as intermediates for preparation of prostaglandin derivatives represented by the general formula (I).

EXAMPLES

The present invention will be explained more specifically with reference to the following examples. However, the scope of the present invention is not limited to these examples.

Example 1

Synthesis of [3aR-(3aα,4α,5α,6aα)]-hexahydro-2-oxo-4-(5-phenyl-3-oxopent-1-phenyl)-5-benzoyloxy-2H-cyclopenta[b]furan [compound of the formula (IV) wherein X is benzoyl Group]

A solution of 1,3-diisopropylcarbodiimide (13.7 g) in dimethyl sulfoxide (38 mL) contained in a nitrogen-substituted flask was added dropwise with a solution of [3aR-(3aα,4α,5α,6aα)]-5-(benzoyloxy)hexahydro-4-(hydroxymethyl)-2H-cyclopenta[b]furan-2-one [compound of the formula (II) (X is benzoyl), 14.9 g] and orthophosphoric acid (1.1 g) in dimethyl sulfoxide. The mixture was stirred at about 30° C. for 2 hours, and then added with methylene chloride, and the deposited white solid was removed by filtration. The filtrate washed with water, dried over magnesium sulfate, then filtered, and concentrated to obtain 23.2 g of an aldehyde compound.

A solution of dimethyl (2-oxo-4-phenylbutyl)phosphonate (18.0 g) in tetrahydrofuran was added with lithium chloride (3.0 g) and triethylamine (7.1 g) and stirred. The mixture was added dropwise with a solution of the aldehyde obtained in the previous reaction in methylene chloride (90 mL) under ice cooling, and stirred for 2 hours. After completion of the reaction, the reaction mixture was adjusted to about pH 2 with 2 M hydrochloric acid, and added with water, and the layers were separated. The organic layer was dried over magnesium sulfate, filtered, and concentrated to obtain a crude product. The resulting crude product was subjected to silica gel column chromatography (ethyl acetate/hexane=1/2→ethyl acetate), and crystals deposited after evaporation of the solvent were collected by filtration, and dried to obtain 15.9 g of a product (yield: 73%).

NMR δ 5.07 (m, 1H), 5.28 (m, 1H), 6.20 (d, 1H), 6.65 (dd, 1H), 7.16-7.30 (m, 5H), 7.42-7.47 (m, 2H), 7.55-7.60 (m, 1H), 7.96-8.00 (m, 2H)

Example 2

Synthesis of [3aR-(3aα,4α,5α,6aα)]-hexahydro-2-oxo-4-[(3S)-5-phenyl-3-hydroxypent-1-phenyl]-5-benzoyloxy-2H-cyclopenta[b]furan [compound of the formula (V) wherein X is benzoyl Group]

Tetrahydrofuran (150 mL) contained in a nitrogen-substituted flask was added with lithium aluminum hydride (4.7 g), and stirred at 60° C. The suspension was ice cooled, added dropwise with a solution of ethanol (5.7 g) in tetrahydrofuran, and then added dropwise with a solution of (S)-1,1-bi-2-naphthol (35.4 g) in tetrahydrofuran (40 mL). The mixture was stirred at room temperature, then cooled on a dry ice-methanol bath, and added dropwise with a solution of [3aR-(3aα,4α,5 α,6aα)]-hexahydro-2-oxo-4-(5-phenyl-3-oxopent-1-phenyl)-5-benzoyloxy-2H-cyclopenta[b]furan (10.0 g) obtained in Example 1 in tetrahydrofuran (60 mL). After completion of the reaction, the reaction mixture was added with methanol (14 mL), warmed to 0° C. and added with water (14 mL). This solution was added to saturated aqueous sodium hydrogentartrate, and extracted with ethyl acetate, and the organic layer washed with saturated brine, dried over magnesium sulfate, filtered, and concentrated to obtain a product. This product was subjected to silica gel column chromatography (methylene chloride/ethyl acetate) to obtain 5.9 g of a purified product.

NMR δ 4.12 (m, 1H), 5.03 (m, 1H), 5.24 (m, 1H), 5.65 (m, 2H), 7.12-7.29 (m, 5H), 7.40-7.45 (m, 2H), 7.53-7.58 (m, 1H), 7.97-8.00 (m, 2H)

Example 3

Synthesis of [3aR-(3aα,4α,5α,6aα)]-hexahydro-2-oxo-4-[(3R)-5-phenyl-3-hydroxypentyl]-5-benzoyloxy-2H-cyclopenta[b]furan [compound of the formula (VI) wherein X is benzoyl group]

A solution of [3aR-(3aα,4α,5α,6aα)]-hexahydro-2-oxo-4-[(3S)-5-phenyl-3-hydroxypent-1-phenyl]-5-benzoyloxy-2H-cyclopenta[b]furan (5.9 g) obtained in Example 2 in tetrahydrofuran (150 mL) contained in a nitrogen-substituted flask was added with triethylamine (3 mL) and palladium/carbon (0.6 g). The atmosphere was replaced with hydrogen, and then the mixture was stirred at room temperature for 2 hours. The palladium/carbon was removed by filtration, and the filtrate was concentrated to obtain 6.2 g of a product.

NMR δ 3.66 (m, 1H), 5.06 (m, 1H), 5.25 (m, 1H), 7.16-7.29 (m, 5H), 7.40-7.45 (m, 2H), 7.52-7.57 (m, 1H), 7.96-8.00 (m, 2H)

Example 4

Synthesis of [3aR-(3aα,4α,5α,6aα)]-hexahydro-2-oxo-4-[(3R)-5-phenyl-3-hydroxypentyl]-5-hydroxy-2H-cyclopenta[b]furan [compound of the formula (VII)]

A solution of [3aR-(3aα,4α,5α,6aα)]-hexahydro-2-oxo-4-[(3R)-5-phenyl-3-hydroxypentyl]-5-benzoyloxy-2H-cyclopenta[b]furan (6.2 g) obtained in Example 3 in methanol (70 mL) and potassium carbonate (20.2 g) were added to a flask, and stirred at room temperature for 1 hour. The reaction mixture was adjusted to pH 2 with hydrochloric acid, and methanol was evaporated. Then, the reaction mixture was extracted with ethyl acetate, and the organic layer washed with saturated brine, dried over magnesium sulfate, filtered and concentrated to obtain a product. The resulting product was subjected to silica gel column chromatography (ethyl acetate/n-hexane) to obtain 3.9 g of a purified product.

NMR δ 3.60 (m, 1H), 3.97 (m, 1H), 4.92 (m, 1H), 7.18-7.30 (m, 5H)

Example 5

Synthesis of [3aR-(3aα,4α,5α,6aα)]-hexahydro-2-oxo-4-[(3R)-5-phenyl-3-tetrahydropyranyloxypentyl]-5-tetrahydropyranyloxy-2H-cyclopenta[b]furan [compound of the formula (VIII) wherein P is tetrahydropyranyl group]

A solution of [3aR-(3aα,4α,5α,6aα)]-hexahydro-2-oxo-4-[(3R)-5-phenyl-3-hydroxypentyl]-5-hydroxy-2H-cyclopenta[b]furan (3.9 g) obtained in Example 4 in methylene chloride (60 mL) contained in a nitrogen-substituted flask was added with dihydropyrane (2.7 g) and pyridinium p-toluenesulfonate (0.3 g), and the mixture was stirred at room temperature for 3 hours. The reaction mixture was poured into aqueous saturated sodium hydrogencarbonate, the layers were separated, and then the aqueous layer was extracted with methylene chloride. The organic layer was washed with saturated brine, then dried over magnesium sulfate, filtered, and concentrated to obtain 6.0 g of a product.

NMR δ 3.48-4.11 (m, 6H), 4.65 (m, 2H), 4.97 (m, 1H), 7.16-7.30 (m, 5H)

Example 6

Synthesis of [3aR-(3aα,4α,5α,6aα)]-hexahydro-2-hydroxy-4-[(3R)-5-phenyl-3-tetrahydropyranyloxypentyl]-5-tetrahydropyranyloxy-2H-cyclopenta[b]furan [compound of the formula (IX) wherein P is tetrahydropyranyl group]

A solution of [3aR-(3aα,4α,5α,6aα)]-hexahydro-2-oxo-4-[(3R)-5-phenyl-3-tetrahydropyranyloxypentyl]-5-tetrahydropyranyloxy-2H-cyclopenta[b]furan (6.0 g) obtained in Example 5 in toluene (60 mL) contained in a nitrogen-substituted flask was added dropwise with a solution of sodium bis(2-methoxyethoxy)aluminum hydride (3.1 g) in toluene at −78° C. The mixture in which the reaction was completed was added dropwise with methanol (12 mL), warmed to 0° C., and then added with water, and insoluble matters were removed by filtration. After the layers of the filtrate were separated, the aqueous layer was extracted with toluene, and the organic layer washed with saturated brine, dried over magnesium sulfate, filtered, and concentrated to obtain a product. The resulting product was subjected to silica gel column chromatography (ethyl acetate/n-hexane) to obtain 5.3 g of a purified product.

NMR δ 3.46-4.16 (m, 6H), 4.63 (m, 3H), 5.62 (m, 1H), 7.16-7.30 (m, 5H)

Example 7

Synthesis of 11,15-bistetrahydropyranyloxy-13,14-dihydro-17-phenyl-18,19,20-trinor-PGF2α [compound of the formula (X) wherein P is tetrahydropyranyl group]

A solution of potassium t-butoxide (6.6 g) in dimethyl sulfoxide (37 mL) contained in a nitrogen-substituted flask was added with 4-carboxybutyl-triphenylphosphonium bromide (8.6 g). Then, the mixture was added dropwise with a solution of [3aR-(3aα,4α,5α,6aα)]-hexahydro-2-hydroxy-4-[(3R)-5-phenyl-3-tetrahydropyranyloxypentyl]-5-tetrahydropyranyloxy-2H-cyclopenta[b]furan (4.6 g) obtained in Example 6 in dimethyl sulfoxide, and the mixture was stirred at room temperature for 2.5 hours. The mixture in which the reaction was completed was poured into ice water, added with 6 M hydrochloric acid (6 mL), and extracted with methylene chloride. The organic layer washed with saturated brine, dried over magnesium sulfate, filtered and concentrated, and the concentrated residue was subjected to silica gel column chromatography (ethyl acetate/n-hexane) to obtain 3.9 g of a purified product.

NMR δ 3.50-4.16 (m, 7H), 4.63-4.72 (m, 2H), 5.37 (m, 1H), 5.52 (m, 1H), 7.16-7.30 (m, 5H)

Example 8

Synthesis of isopropyl 11,15-bistetrahydropyranyloxy-13,14-dihydro-17-phenyl-18,19,20-trinor-PGF2α [compound of the formula (XI) wherein P is tetrahydropyranyl group]

A solution of 11,15-bistetrahydropyranyloxy-13,14-dihydro-17-phenyl-18,19,20-trinor-PGF2α (2.9 g) obtained in Example 7 in dimethylformamide (30 mL) contained in a nitrogen-substituted flask was added with cesium carbonate (3.3 g) and isopropyl iodide (2.6 g), and the mixture was stirred at 35° C. for 2 hours. The reaction mixture was poured into 10% aqueous ammonium chloride, and extracted with toluene. The organic layer washed with saturated brine, dried over magnesium sulfate, filtered, and concentrated to obtain a product. The product was subjected to silica gel column chromatography (ethyl acetate/n-hexane) to obtain 2.7 g of a purified product.

NMR δ 1.22 (d, 6H), 3.49-4.16 (m, 7H), 4.65 (m, 2H), 5.00 (m, 1H), 5.43 (m, 2H), 7.17-7.30 (m, 5H)

Example 9

Synthesis of isopropyl 13,14-dihydro-17-phenyl-18,19,20-trinor-PGF2α [compound of the formula (I) wherein $R^1$ is isopropyl group=latanoprost]

A solution of isopropyl 11,15-bistetrahydropyranyloxy-13,14-dihydro-17-phenyl-18,19,20-trinor-PGF2α (1.5 g) obtained in Example 8 in isopropanol (45 mL) was added with p-toluenesulfonic acid (0.05 g), and the mixture was stirred at 40° C. for 5 hours. After completion of the reaction, isopropanol was evaporated to obtain a product. The product was purified by silica gel column chromatography to obtain 0.87 g of latanoprost.

NMR δ 1.22 (d, 6H), 2.28 (t, 2H), 3.65 (m, 1H), 3.93 (m, 1H), 4.15 (m, 1H), 4.99 (qq, 1H), 5.42 (m, 2H), 7.25 (m, 5H)

What is claimed is:

1. A method for preparing a prostaglandin derivative represented by the following general formula (I):

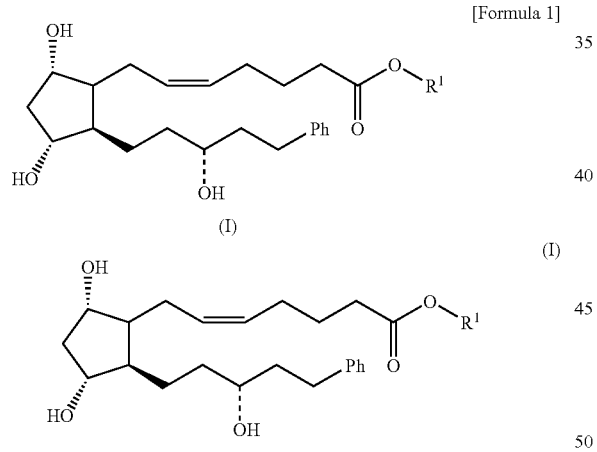

wherein Ph represents phenyl group, $R^1$ represents a $C_{1-7}$ alkyl group, a $C_{1-7}$ alkenyl group, phenyl group, or benzyl group, which comprises:

(1) converting a compound represented by the following formula (II), wherein

X represents a protective group selected from the group consisting of an aroyl group having 0 to 3 substituents, a trialkylsilyl group, and a triarylsilyl group, wherein the substituents of the aroyl group are selected from the group consisting of a halogen atom, a $C_{1-6}$ alkyl group and a $C_{6-12}$ aryl group into a compound represented by the following formula (IV) by oxidizing the compound of the formula (II) into an aldehyde and then reacting the aldehyde with a phosphonic acid ester represented by the following formula (III) ($R^2$ represents a $C_{1-6}$ alkyl group or a $C_{6-12}$ aryl group);

(2) converting the compound represented by the following formula (IV) into a compound represented by the following formula (V) by reducing the oxo group on the side chain of the compound of the formula (IV) using (S)-1,1'-binaphthyl-2-2'-dioxyaluminum hydride as a reducing agent;

(3) converting the compound represented by the following formula (V) into a compound represented by the following formula (VI) by hydrogenating the compound of the formula (V);

(4) converting the compound represented by the following formula (VI) into a compound represented by the following formula (VII) by removing the protective group X of the compound of the formula (VI);

(5) converting the compound represented by the following formula (VII) into a compound represented by the following formula (VIII) by protecting the hydroxyl groups of the compound of the formula (VII) with protective groups P, wherein the protective group P is a tetrahydropyranyl group;

(6) converting the compound represented by the following formula (VIII) into a compound represented by the following formula (IX) by reducing the oxo group on the lactone ring of the compound of the formula (VIII);

(7) converting the compound represented by the following formula (IX) into a compound represented by the following formula (X) by reacting the compound of the formula (IX) with a 4-carboxybutyltriphenylphosphonium halide; and (8) converting the compound represented by the following formula (X) into a compound represented by the following formula (XI) by esterifying the carboxyl group of the compound of the formula (X) and then removing the protective groups P:

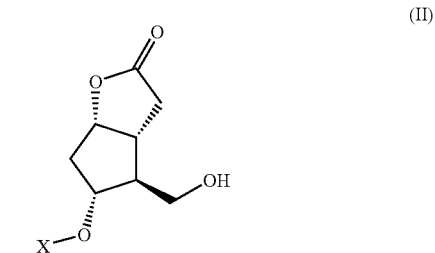

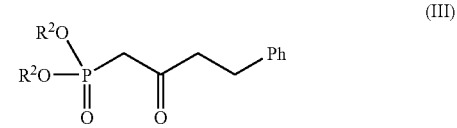

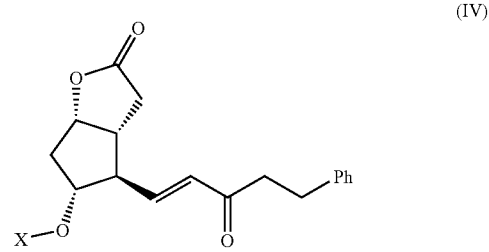

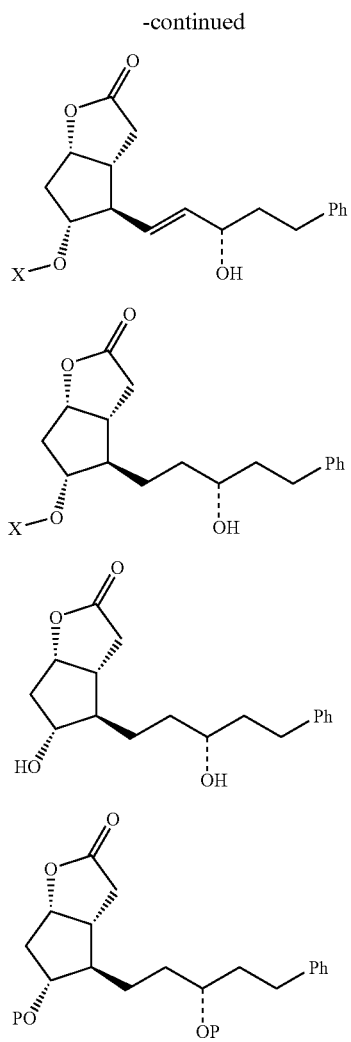
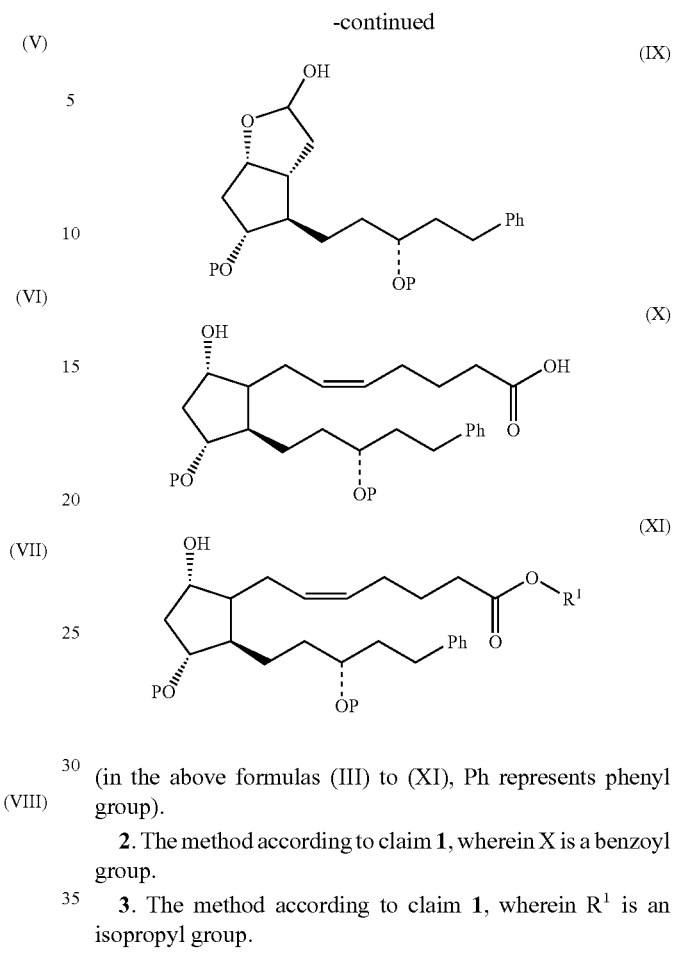
(in the above formulas (III) to (XI), Ph represents phenyl group).
2. The method according to claim 1, wherein X is a benzoyl group.
3. The method according to claim 1, wherein $R^1$ is an isopropyl group.
4. The method according to claim 2, wherein $R^1$ is an isopropyl group.
* * * * *

UNITED STATES PATENT AND TRADEMARK OFFICE
CERTIFICATE OF CORRECTION

PATENT NO. : 7,642,370 B2 Page 1 of 1
APPLICATION NO. : 11/688566
DATED : January 5, 2010
INVENTOR(S) : Noriaki Murata et al.

It is certified that error appears in the above-identified patent and that said Letters Patent is hereby corrected as shown below:

In the claims:

At column 13, line 45, claim 1 of the printed patent, delete second formula

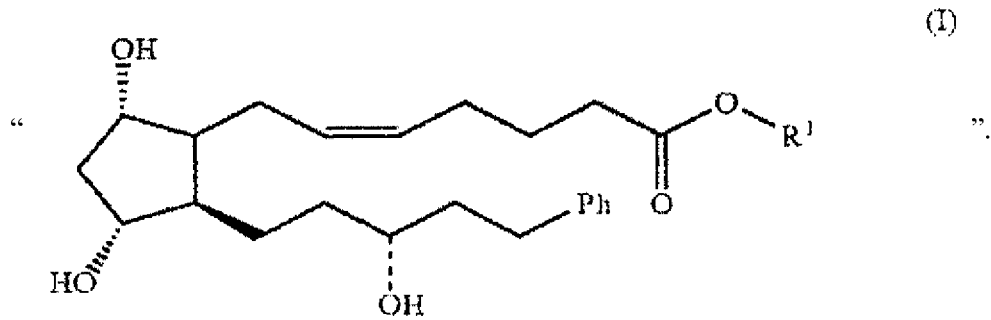

Signed and Sealed this

Seventh Day of September, 2010

David J. Kappos
*Director of the United States Patent and Trademark Office*